United States Patent
Ragusa et al.

(10) Patent No.: US 9,370,615 B2
(45) Date of Patent: Jun. 21, 2016

(54) SYSTEM AND METHOD FOR AUTOMATED SEPARATION OF WHOLE BLOOD

(71) Applicant: Haemonetics Corporation, Braintree, MA (US)

(72) Inventors: Michael Ragusa, Hingham, MA (US); Shiven Ruparel, Waltham, MA (US); Dominique Uhlmann, Abington, MA (US)

(73) Assignee: Haemonetics Corporation, Braintree, MA (US)

( * ) Notice: Subject to any disclaimer, the term of this patent is extended or adjusted under 35 U.S.C. 154(b) by 272 days.

(21) Appl. No.: 14/046,257

(22) Filed: Oct. 4, 2013

(65) Prior Publication Data

US 2014/0039373 A1 Feb. 6, 2014

Related U.S. Application Data

(63) Continuation of application No. PCT/US2012/036554, filed on May 4, 2012.

(60) Provisional application No. 61/483,426, filed on May 6, 2011.

(51) Int. Cl.
*A61M 37/00* (2006.01)
*A61M 1/38* (2006.01)
(Continued)

(52) U.S. Cl.
CPC ............ *A61M 1/38* (2013.01); *A61M 1/0209* (2013.01); *A61M 1/3672* (2013.01); *A61M 1/3693* (2013.01); *B04B 5/0442* (2013.01); *B04B 11/04* (2013.01); *A61M 1/0231* (2014.02)

(58) Field of Classification Search
CPC ... A61M 1/38; A61M 1/0209; A61M 1/3672; A61M 1/3693; A61M 1/3496
USPC ....................................... 604/5.01
See application file for complete search history.

(56) References Cited

U.S. PATENT DOCUMENTS

| | | | |
|---|---|---|---|
| 3,145,713 A | 8/1964 | Latham, Jr. | 128/214 |
| 4,943,273 A | 7/1990 | Pages | 494/41 |

(Continued)

FOREIGN PATENT DOCUMENTS

| | | |
|---|---|---|
| CN | 2927990 Y | 8/2007 |
| CN | 102046224 A | 5/2011 |
| WO | WO 2009/129131 | 10/2009 |

OTHER PUBLICATIONS

State Intellectual Property Office of the People's Republic of China, Official Action—Application No. 201280022014.2, dated Jan. 6, 2015, 17 pages.

(Continued)

*Primary Examiner* — Leslie Deak
(74) *Attorney, Agent, or Firm* — Sunstein Kann Murphy & Timbers LLP (57) ABSTRACT

An apparatus for separating whole blood includes an access device for drawing whole blood from a source, a blood component separation device, a draw line, a draw pump, and a controller. The blood component separation device separates the drawn whole blood into a first blood component and a second blood component. The draw line fluidly connects the access device and the blood component separation device, and the draw pump draws whole blood from the source through the access device and draw line and into the blood component separation device. The controller controls fluid flow through the apparatus and operation of the draw pump. The controller also monitors the total volume of whole blood drawn from the source and the total volume of first blood component collected. The controller stops the draw pump when the first of a target whole blood volume is withdrawn or a target volume of first blood component is collected.

49 Claims, 5 Drawing Sheets

(51) Int. Cl.
*A61M 1/02* (2006.01)
*A61M 1/36* (2006.01)
*B04B 5/04* (2006.01)
*B04B 11/04* (2006.01)

(56) References Cited

U.S. PATENT DOCUMENTS

| | | | |
|---|---|---|---|
| 4,983,158 A | 1/1991 | Headley | 494/41 |
| 5,478,479 A | 12/1995 | Herrig | 210/745 |
| 5,651,766 A | 7/1997 | Kingsley et al. | 604/6 |
| 5,720,921 A | 2/1998 | Meserol | 422/44 |
| 5,779,660 A | 7/1998 | Kingsley et al. | 604/6 |
| 5,853,382 A | 12/1998 | Kingsley et al. | 604/4 |
| 5,882,289 A | 3/1999 | Sakota et al. | 494/41 |
| 6,099,491 A | 8/2000 | Headley et al. | 604/4 |
| 6,743,192 B1 * | 6/2004 | Sakota | A61M 1/3693 210/195.1 |
| 7,037,428 B1 | 5/2006 | Robinson et al. | 210/416.1 |
| 2001/0006810 A1 | 7/2001 | Brown | 435/286.1 |
| 2002/0058030 A1 * | 5/2002 | Monroy | A61M 1/3633 424/140.1 |
| 2003/0125881 A1 * | 7/2003 | Ryan | A61M 1/3496 702/19 |
| 2003/0233064 A1 | 12/2003 | Arm et al. | 604/4.01 |
| 2004/0127840 A1 | 7/2004 | Gara et al. | 604/4.01 |
| 2007/0012623 A1 * | 1/2007 | Robinson | A61M 1/3693 210/647 |
| 2009/0259163 A1 | 10/2009 | Pages et al. | 604/6.02 |
| 2009/0259164 A1 | 10/2009 | Pages et al. | 604/6.04 |
| 2014/0045672 A1 | 2/2014 | Galavotti et al. | 494/44 |
| 2015/0273132 A1 | 10/2015 | Ragusa et al. | |

OTHER PUBLICATIONS

State Intellectual Property Office of the People's Republic of China, Official Action (Notification of the First Office Action)—Application No. 201280022014.2, dated Jan. 6, 2015, 10 pages [English Translation].

State Intellectual Property Office of the People's Republic of China, Official Action—Application No. 201280022014.2, dated Aug. 6, 2015, 15 pages.

State Intellectual Property Office of the People's Republic of China, Official Action (Notification of the Second Office Action)—Application No. 201280022014.2, dated Aug. 6, 2015, 4 pages [English Translation].

European Patent Office, Examination Report—Application No. 12782429.0, dated Jul. 14, 2015, 6 pages.

Blaine R. Copenheaver, Authorized officer United States Patent and Trademark Office (International Searching Authority), International Search Report—Application No. PCT/US2012/036554, mailed Aug. 17, 2012, together with the Written Opinion of the International Searching Authority, 15 pages.

* cited by examiner

SYSTEM AND METHOD FOR AUTOMATED SEPARATION OF WHOLE BLOOD

PRIORITY

This application is a continuation of Patent Cooperation Treaty application PCT/US2012/036554, entitled "System and Method for Automated Separation of Whole Blood," filed May 4, 2012, and naming Michael Ragusa, Shiven Ruparel, and Dominique Uhlmann as inventors, the disclosure of which is incorporated herein, in its entirety, by reference.

Patent Cooperation Treaty application PCT/US2012/036554, in turn, claims priority from U.S. Provisional Patent Application Ser. No. 61/483,426, filed May 6, 2011, entitled, "System and Method for Automated Separation of Whole Blood," and naming Michael Ragusa, Shiven Ruparel, and Dominique Uhlmann as inventors, the disclosure of which is incorporated herein, in its entirety, by reference.

TECHNICAL FIELD

The present invention relates to systems and methods for blood processing, and more particularly to systems and methods for automated separation of whole blood.

BACKGROUND ART

In prior art methods for collecting and separating whole blood, a technician places a needle into a vein in the donor's arm, causing whole blood to flow (e.g., by gravity) into a storage bag which may hold a quantity of anticoagulant solution to prevent the collected blood from clotting. After collecting a fixed volume of whole blood (e.g., approximately 400 ml+/−10%) from the donor, the technician removes the needle and the donor is free to leave. The technician then repeats the blood collection step for a number of donors with varying hematocrits (the ratio of the volume of packed red blood cells to the volume of whole blood—typically 38% to 60%). After collecting whole blood from each of the donors, the technician then transports the whole blood bags to a laboratory for processing.

Once in the laboratory, the technician places the whole blood bags into a large centrifuge which spins at a high rate of speed to separate the whole blood within the bags into its constituent components. The technician then removes the bags from the centrifuge (taking care not to re-mix the separated blood components) and transfers the bags to a device such as an expressor to remove plasma from the bag (e.g., leaving red blood cells remaining in the bag). After some additional processing, each of the individual components may then be stored separately.

As one may expect, prior art methods such as those described above are labor intensive, and require numerous manual manipulations. Additionally, because the whole blood must be transported to the lab, the whole blood must be stored for up to several hours prior to processing.

SUMMARY OF THE EMBODIMENTS

In accordance with one embodiment of the present invention, an apparatus for separating whole blood includes an access device for drawing whole blood from a source (e.g., a subject, donor, whole blood container, etc.), a blood component separation device, a draw line, a draw pump, and a controller. The blood component separation device is configured to separate the drawn whole blood into a first blood component and a second blood component.

The draw line may fluidly connect the access device and the blood component separation device. The draw pump may draw whole blood from the source, through the access device and draw line, and into the blood component separation device. The controller may control fluid flow through the apparatus and may control the operation of the draw pump. The controller may also monitor a total volume of whole blood drawn from the source and a total volume of first blood component collected. The controller may stop the draw pump when the first of a target whole blood volume (e.g., 400 ml) is withdrawn or a target volume of first blood component is collected.

The apparatus may also include an optical sensor that monitors fluid flowing out of the blood component separation device and outputs a signal representative of the fluid. The controller may be in communication with the optical sensor and receive the output signal from the optical sensor. The controller may also control operation of the draw pump based, at least in part, upon the output signal, and determine the total volume of whole blood drawn from the source based upon a number of revolutions of the draw pump.

Additionally, the blood component separation device may include a centrifugal bowl that has a volume sufficient to hold the target volume of first blood component. Furthermore, if the whole blood storage container still contains whole blood, the controller may restart the draw pump after a target volume of first blood component is collected. For example, the controller may calculate a volume of first blood component remaining in the whole blood storage container based, at least in part, upon a hematocrit value of the whole blood, and then transfer a volume of first blood component from the blood component separation device to the first blood component storage container. The volume of first blood component transferred may be based upon the calculated volume of first blood component remaining in the whole blood storage container. The controller may then restart the draw pump after the blood component separation device is emptied and/or the volume of first blood component is transferred.

The system/apparatus may include a user input device that allows a user to input a hematocrit value of the drawn whole blood. The controller may control the speed of the separation device based, at least in part, upon the hematocrit value. The apparatus/system may also include an additive solution container, an additive solution line fluidly connecting the additive solution container and the separation device, and a second pump. The second pump may draw additive solution from the additive solution container, through the additive solution line, and into the blood component separation device to wash the first blood component within the blood component separation device.

In accordance with further embodiments, a method for separating whole blood may include (1) drawing whole blood from a source, (2) introducing anticoagulant into the whole blood drawn from the source, (3) introducing, using a draw pump, the anticoagulated whole blood into a separation chamber which separates the whole blood into a first blood component and a second blood component, (4) monitoring a total volume of whole blood drawn from the source and a total volume of first blood component collected within the separation chamber to determine when a target whole blood volume is drawn and when a target volume of first blood component is collected, and (5) stopping, using a controller, the draw of whole blood from the source when the first of the target whole blood volume and target volume of first blood component is reached. The method may also include monitoring, using an optical sensor, fluid flowing out of the blood component separation device. The optical sensor may output a signal representative of the fluid. The controller may receive the output signal and control the operation of the draw pump based, at least in part, upon the output signal.

In some embodiments, the controller determines the total volume of whole blood drawn from the source based upon a number of revolutions of the draw pump. The source may be a donor or a whole blood storage container (e.g., containing the target whole blood volume), and the blood component separation device may include a centrifugal bowl having a volume sufficient to hold the target volume of first blood component. In additional embodiments, the method may also include drawing additive solution from an additive solution container and into the blood component separation device. The additive solution may wash the first blood component within the blood component separation device as it enters the separation device.

The method may also include restarting the draw pump after a target volume of first blood component is collected and if the whole blood storage container still contains whole blood. The controller may calculate a volume of first blood component remaining in the whole blood storage container based, at least in part, upon a hematocrit value of the whole blood. The controller may then transfer a volume of first blood component from the blood component separation device to the first blood component storage container. The volume of first blood component transferred may be based upon the calculated volume of first blood component remaining in the whole blood storage container. The controller may restart the draw pump after the first blood component is transferred from the separation device. Additionally, the controller may control the speed of the blood component separation device based, at least in part, upon the hematocrit value of the drawn whole blood.

In accordance with further embodiments, a system for separating whole blood may include (1) means for drawing whole blood from a source, (2) means for introducing anticoagulant into the whole blood drawn from the source, (3) a blood component separation device for separating the drawn whole blood into a first blood component and a second blood component, (4) means for introducing the anticoagulated whole blood into the separation device, (5) means for monitoring a total volume of whole blood drawn from the source and a total volume of first blood component collected in the separation device, and (6) a controlling means, in communication with the means for monitoring. The controlling means determines when a target whole blood volume is drawn and when a target volume of first blood component is collected. The controlling means may also be configured to stop the draw of whole blood from the source when the first of the target whole blood volume and target volume of first blood component is reached.

The system may also include a sensing means for monitoring fluid flowing out of the blood component separation device. The sensing means may output a signal representative of the fluid. The controlling means may receive the output signal and control operation of the means for drawing based, at least in part, upon the output signal. The means for drawing whole blood may include a draw pump, and the controlling means may determine the total volume of whole blood drawn based upon the number of revolutions of the draw pump. The blood component separation device may include a centrifugal bowl that has a volume sufficient to hold the target volume of first blood component.

In some embodiments, the source may be a whole blood storage container containing a volume of whole blood that is substantially equal to the target whole blood volume. The controlling means may be configured to restart the means for drawing after the target volume of first blood component is collected in the separation chamber and if the whole blood storage container still contains whole blood. For example, the controlling means may restart the means for drawing after the blood component separation device is emptied. Additionally or alternatively, the controlling means may calculate a volume of first blood component remaining in the whole blood storage container based, at least in part, upon a hematocrit value of the whole blood. The controlling means may then transfer a volume of first blood component from the blood component separation device to the first blood component storage container. The volume of first blood component transferred may be based upon the calculated volume of first blood component remaining in the whole blood storage container.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
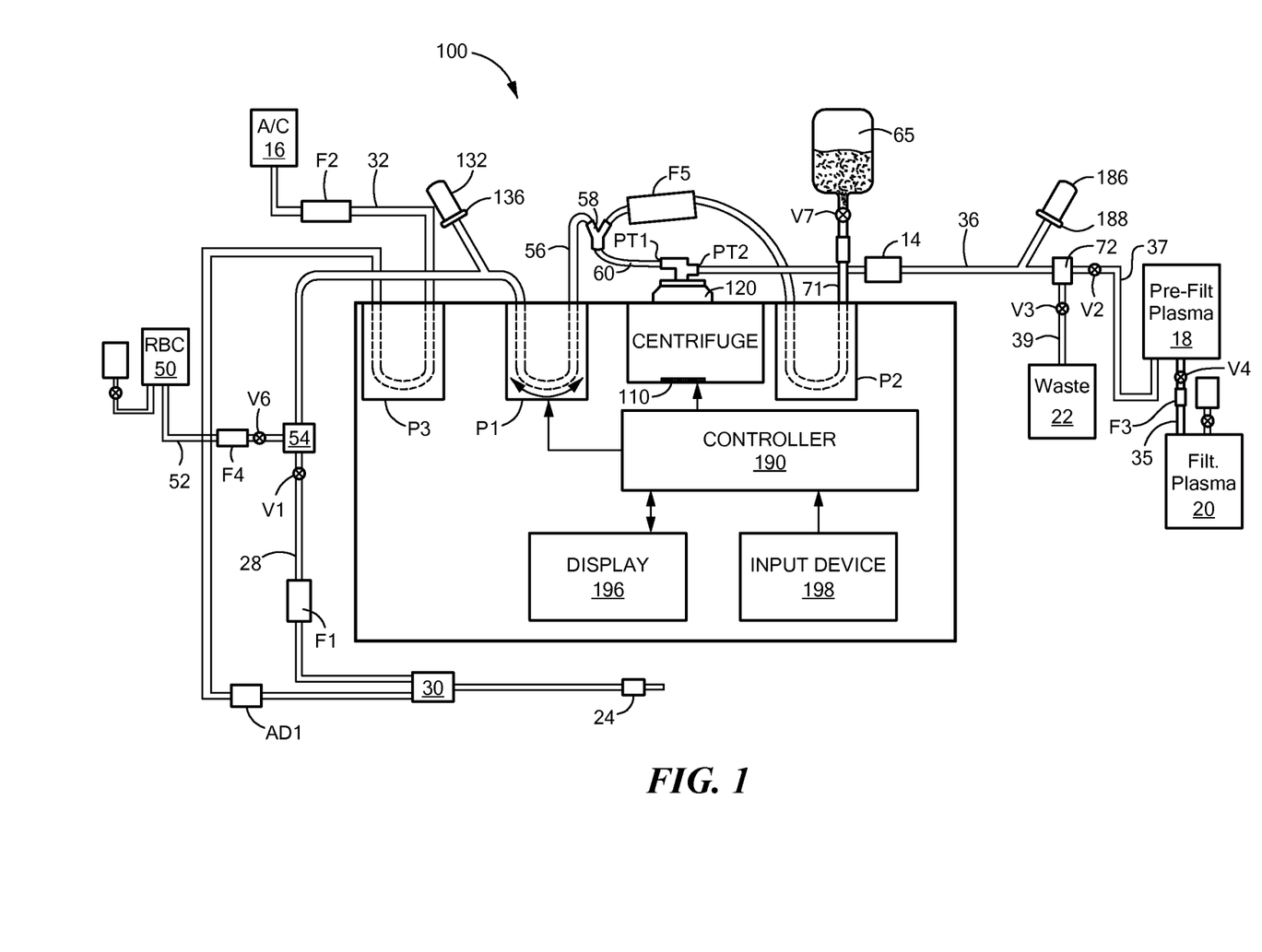
FIG. 1 is a schematic diagram of an automated whole blood separation system, in accordance with one embodiment of the present invention.
Figure 2:
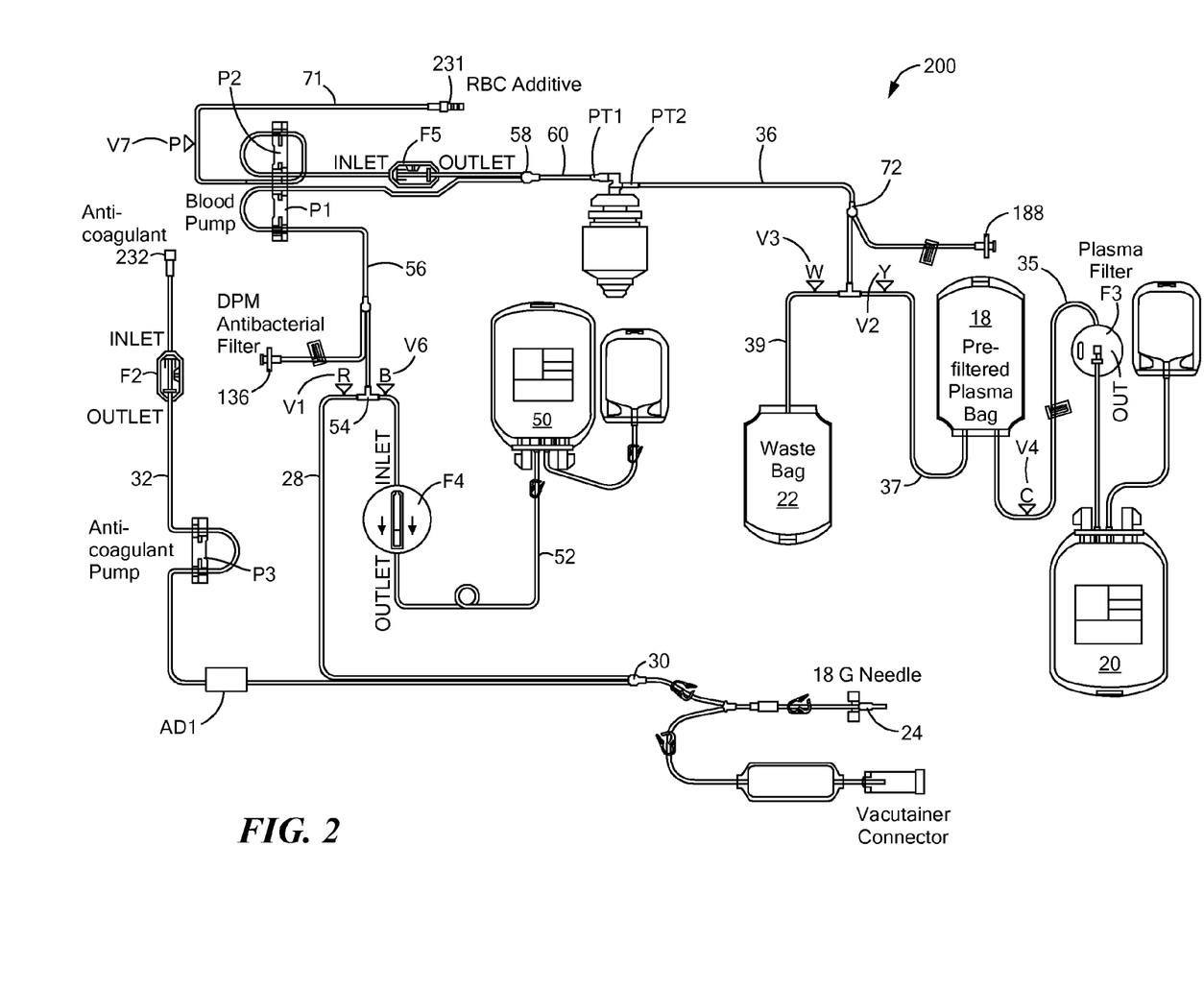
FIG. 2 is a schematic diagram of a disposable set for use with the system of FIG. 1, in accordance with one embodiment of the present invention.

Referring to FIGS. 1 and 2, an automated whole blood collection system 100 uses a centrifuge 110, such as the centrifuge bowl described within U.S. Pat. No. 4,983,158, which is hereby incorporated by reference, to separate whole blood into its constituent components. Other types of separation chambers and devices may be used, such as, without limitation, a standard Latham type centrifuge, as described in U.S. Pat. Nos. 3,145,713 and 5,882,289, which are hereby incorporated by reference. The centrifuge 110 includes a rotating bowl 120 and stationary input and output ports PT1 and PT2 that are typically closely coupled to the bowl interior by a rotary seal 74 (see FIG. 3). Although the material and size of the bowl 120 may vary depending upon the application and amount of whole blood to be processed and/or red blood cells to be collected, preferred embodiments of the present invention utilize bowls having volumes ranging from preferably 200 to 300 ml, more preferably from 210 to 275 ml, more preferably from 220 to 230 ml, and most preferably about 225 ml. It should be noted that other bowl sizes may be utilized. For example, the bowl may be smaller than 210 ml, or larger than 300 ml. A preferable bowl material is K resin.

Figure 3:
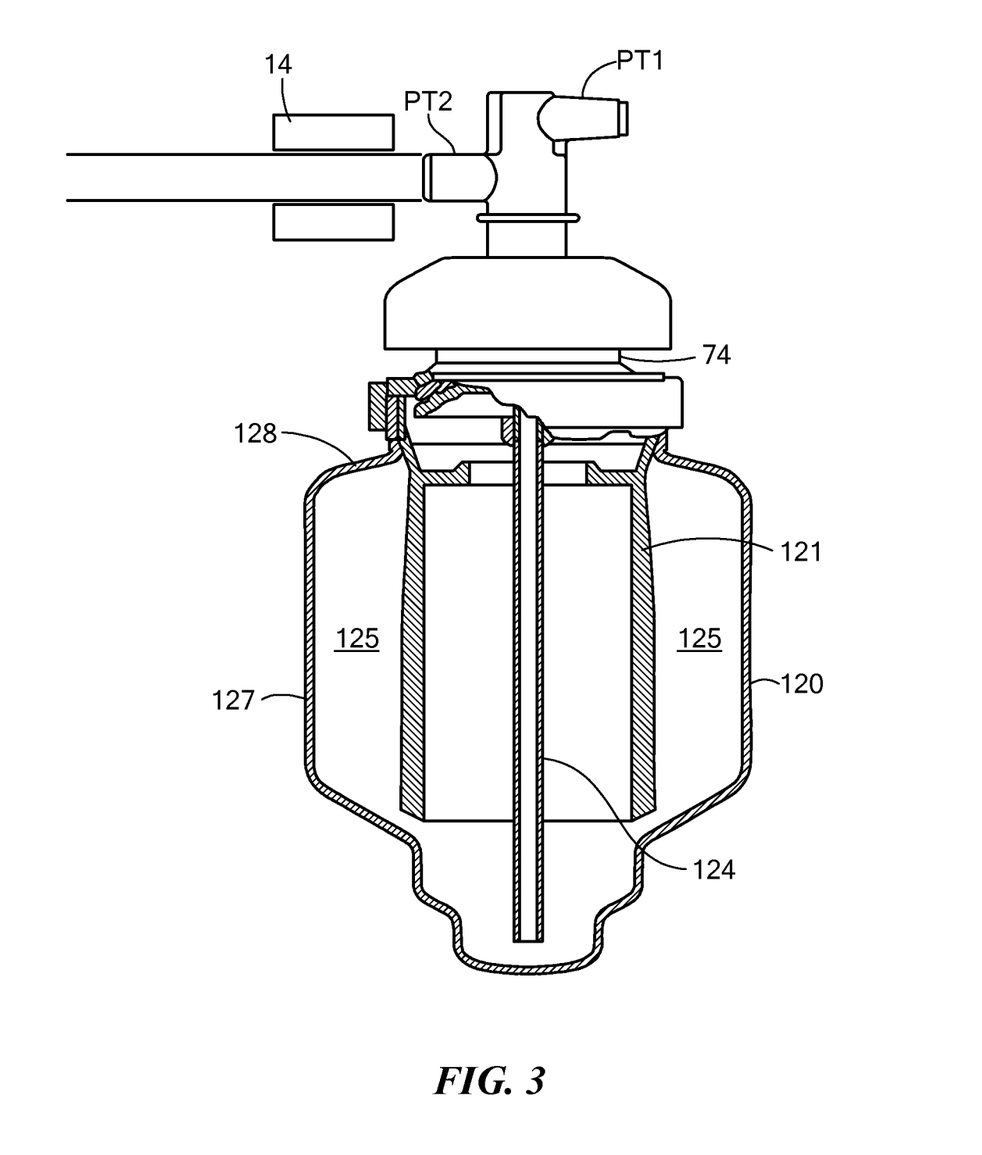
FIG. 3 schematically shows a side view of a centrifuge bowl for use with the whole blood separation system of FIG. 1, in accordance with some embodiments of the present invention.

As shown in FIG. 3, in some embodiments, the centrifuge bowl 120 may include a core 121 located within the interior of the bowl 120, such as the centrifuge bowl described within U.S. Pat. No. 4,943,273, which is hereby incorporated by reference. As fluid to be processed (e.g., whole blood, etc.)

enters the bowl 120 through input port PT1, the fluid flows through feed tube 124 and into the bottom of the bowl 120. The centrifugal forces then force the fluid to flow outwardly and upwardly into separation region 125. As discussed in greater detail below, if the collected blood components (e.g., red blood cells) are to be washed, as the wash solution (or additive solution) enters the bowl 120, the wash solution may similarly flow through the feed tube 124, into the bottom of the bowl 120, and into the separation region 125.

The input port PT1 of the centrifuge bowl 120 is in fluid communication with a venous access devices 24 (e.g., a phlebotomy needle) via a tubes 28, 56 and 60, and Y-connectors 30, 54 and 58 when a valve V1 is open. As discussed in greater detail below, the venous access device 24 may be replaced with a whole blood bag (not shown) in case the whole blood is to be first pooled and then supplied (or otherwise collected/stored prior to processing). The tube 28 has compatibility with blood, as is all the tubing in the system 100. The outlet port PT2 of the centrifuge 110/bowl 120 is selectively coupled by a tube 36, a valve V2, connector 72, and a tube 37 with a first container 18 labeled pre-filtered plasma. A second container 22 labeled waste is selectively coupled to the outlet port PT2 via the tube 36, a valve V3 and a tube 39. Additionally, a third container 20 (e.g., for filtered plasma) may be selectively coupled to the pre-filtered plasma container 18 via a tube 35, a valve V4 and a filter F3. Each of the containers 18/20/22 may be suspended by weight scales (not shown).

A bag or container 16 for storing an anticoagulant is in fluid communication with the venous access device/phlebotomy needle 24 via a bacteria filter F2, a tube 32, and the Y-connector 30. The tube 32 may also include an air detector AD1 that detects the presence of air bubbles within the anticoagulant line 32. The bacteria filter F2 prevents any bacteria in the anticoagulant container 16 (or introduced into the container 16/anticoagulant when the container 16 is connected to connection 232) from entering the system. Containers 16, 18, 20, and 22 are preferably plastic bags made of a blood compatible material.

In order to monitor the pressure within the system 100, the system may also include one or more pressure sensors. For example, the system 100 may include a pressure sensor on tube 56 to measure the pressure between the pump P1 and the source of whole blood (e.g., the subject or whole blood container). Similarly, the system 100 may also include a pressure sensor connectable to tube 36 to measure the pressure between the centrifuge bowl 120 and the waste container 22/pre-filtered plasma container 18. Positioned between each of the pressure sensors and tubing 32 may be a filter 136/188 (e.g., a 0.2 μm hydrophobic filter and/or anti-bacterial filter) to preserve sterility of the system 100 from the blood and biological material that may be in tubing 32

The filters 136/188 may be located at the end of a tubing line and may include a housing (e.g., a plastic housing) containing a filter membrane. During set-up of the system 100, one end of the filter 132/186 may be inserted into a port located on the system 100 to connect the filter 136/188 with the associated sensor which, in turn, may be contained within the system 100.

The system 100 may also have a red blood cell collection container 50 (RBC container) for storing the red blood cells collected during whole blood processing. The RBC container 50 may be fluidly connected to the bowl 120 via the line 52, filter F4, valve V6, connector 54, line 56, connector 58 and line 60. Like the other containers, the RBC container 50 is also preferably a plastic bag made of blood compatible material. As discussed in greater detail below, after the whole blood processing is complete, red blood cells within the bowl 120 are transferred to the RBC container 50 for storage and/or further processing.

In some embodiments, the system 100 may also include a controller 190 that controls the overall operation of the system 100 and centrifuge 110. For example, the controller 190 may control the operation of peristaltic pumps P1, P2, and P3 as well as, valves V1/V2/V3/V4/V6/V7 to control the direction and duration of flow through the system 100. The controller 190 may also be coupled to a display screen 196 that presents information to a system operator, and an input device 198 that allows the system operator to input information and supply the controller 190 with information. For example, the input device 198 may allow the user to input a target volume of whole blood to withdraw, a target volume of red blood cells to collect, and/or the hematocrit value of the whole blood being drawn into the system 100. As discussed in greater detail below, the controller 190 may control the speed of the centrifuge 110 based, at least in part, upon the hematocrit valve of the whole blood (e.g., the controller may increase the speed for high hematocrit donors). The controller 190 may also receive outputs from the pressure sensors and a line sensor 14. The line sensor 14 may be an optical sensor that detects the presence of blood components passing through the line sensor 14 from the output port PT2.

As shown in FIG. 2, various components may be packaged together as a disposable set 200. For example, the disposable set 200 may include tubes 28/52/56/32/60/36/37/35/39/71, connectors 30/54/5/72, valves V1/V2/V3/V4/V6/V7, the centrifuge bowl 120, filters F1/F2/F3/F4/F5, the waste container 22, the pre-filtered plasma bag 18, the filtered plasma bag 20, and the red blood cell (RBC) storage bag 50. Additionally, the disposable set 200 may also include connection ports for the anticoagulant container 16 and the additive container 65. For example, the disposable set 200 may include a first sterile connection 231 for connecting the red blood cell (RBC) additive solution container 65, and a second sterile connection 232 for connecting the anticoagulant container 16. Prior to starting the whole blood separation procedure, the disposable set 200 may be removed from its packaging and installed into the system 100, as shown in FIG. 1.

Figure 4:
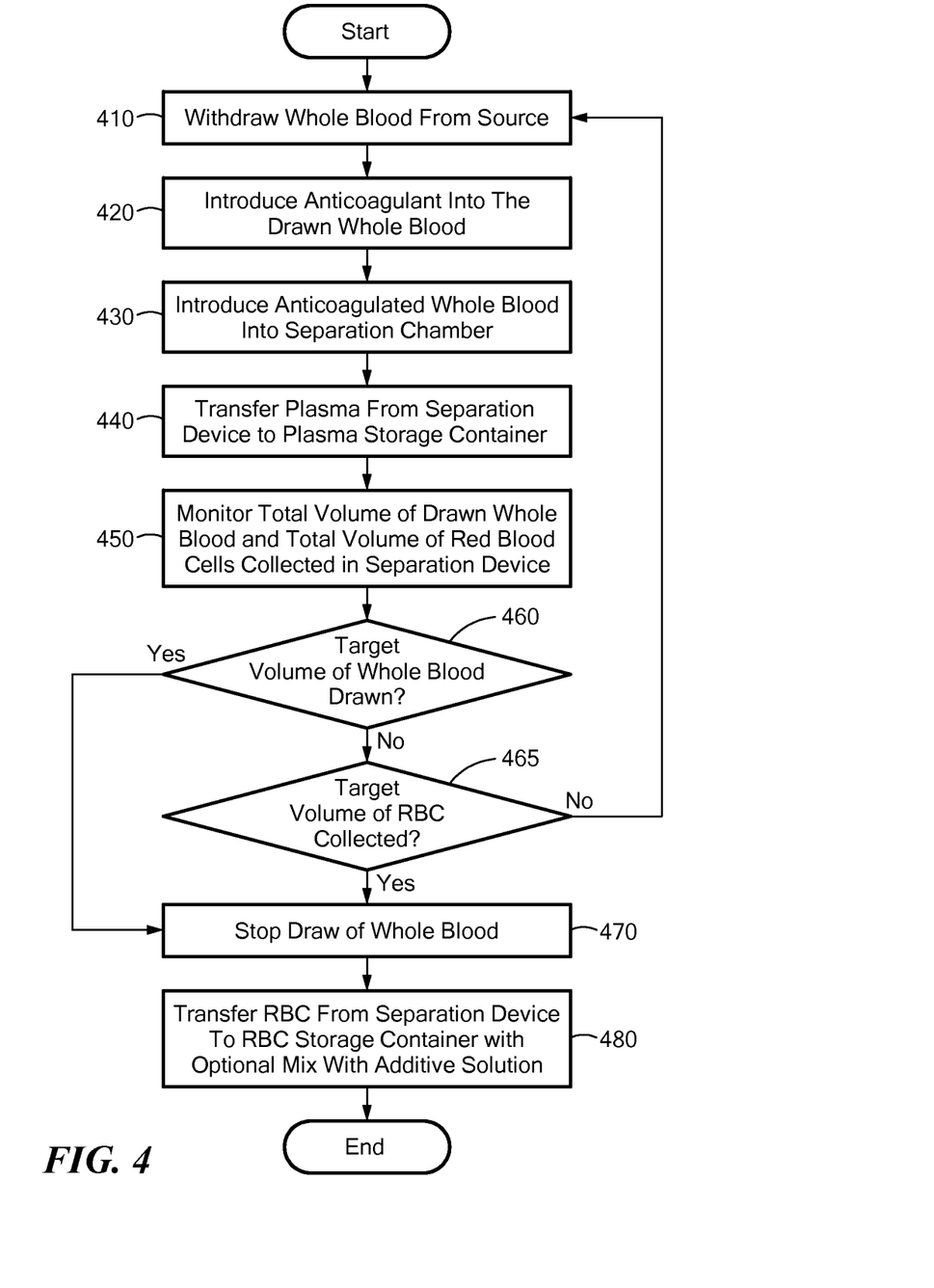
FIG. 4 is a flow chart depicting a method for separating whole blood, in accordance with one embodiment of the present invention.

FIG. 4 is a flowchart depicting a method for separating whole blood in accordance with one embodiment of the present invention. Once the disposable set is installed into the system 100 and the anticoagulant and additive containers 16/65 are connected to their respective sterile connections 232/231, the system may begin to withdraw whole blood from the subject (Step 410). As the whole blood flows through tube 28, the anticoagulant pump P3 mixes the anticoagulant from the container 16 with the whole blood (Step 420) (e.g., anticoagulant may flow through line 32 and mix with the whole blood at connector 30). Additionally, valve V1 is open, allowing the anticoagulated whole blood to pass through the tube 28 and blood filter F1 (optional) before being pumped into the centrifuge bowl 120 through the inlet port PT1. It should be noted that the blood filter F1 is optional, and some embodiments (e.g., single cycle embodiments) may not utilize a blood filter F1.

As discussed above, the whole blood is introduced into the bottom of the bowl 120 though the feed tube 124 (Step 430). Additionally, it should be noted that the ratio of the anticoagulant to whole blood is typically about 1:10, but some embodiments may use other ratios, for example, 1:8. The operation of each of the pumps and valves in the system 100 can be performed in accordance with desired protocols under the control of the controller 190, which may be, for example, a microprocessor.

As the bowl 120 is rotated, centrifugal forces will force the anticoagulated whole blood into the separation region 125 and separate the whole blood into a number of blood components (e.g., red blood cells and plasma). The number of rotations of the bowl 12 can be selected, for example, within a range of 7,000 to 7,500 rpm. The blood is separated into different fractions in accordance with the component densities. The higher density component, i.e., red blood cells, is forced to the outer wall 127 of the bowl 120 while the lower density plasma lies nearer the core 121. A buffy coat may form between the plasma and the RBC. The buffy coat is made up of an inner layer of platelets, a transitional layer of platelets and white blood cells, and an outer layer of white blood cells. The plasma is the component closest to the outlet port from the separation region and is the first fluid component displaced from the bowl 120 via the outlet port PT2 as additional anticoagulated whole blood enters the bowl 120 through the inlet port PT1.

Returning to FIG. 1, as additional whole blood enters the bowl 120, the displaced plasma passes through the line sensor 14, the tube 36, the valve V2 (in the open position), connector 72, and line 37, and enters the pre-filtered plasma container 18 (Step 440). The plasma entering the pre-filtered plasma container 18 may later be filtered through filter F3 and stored in filtered plasma container 20.

As the anticoagulated whole blood is introduced into the bowl 120 and the plasma is displaced (e.g., transferred) to the pre-filtered plasma container 18, the controller may monitor/calculate (1) the total volume of whole blood drawn from the source, and (2) the volume of red blood cells collected within the bowl 120 (Step 450). For example, the controller 190 may calculate the total volume of blood drawn from the source based upon the number of revolutions of the draw pump P1 (e.g., the total volume of whole blood drawn equals the number of revolutions multiplied the known amount of volume per revolution).

Additionally, the controller 190 may also monitor the output signal from the optical sensor 14 to determine when the bowl 120 is full of red blood cells. For example, the optical sensor 14 may monitor the fluid exiting the bowl 120 through the outlet PT2 and detect when the fluid changes from one component to the next. The optical sensor 14 can detect when the fluid exiting the bowl 120 changes from plasma to the buffy coat, and from the buffy coat the red blood cells. Once sensor 14 determines that the fluid exiting the bowl 120 is buffy coat cells, the controller 190 will consider the bowl 120 to be full and the target volume of red blood cells collected.

Additionally or alternatively, the bowl 120 may have a sensor (e.g., an optical sensor) located on a shoulder portion 128 of the bowl 120. The shoulder mounted sensor may monitor each layer of the blood components as they gradually and coaxially advance toward the core 121 from the outer wall 127 of the bowl 120. The shoulder sensor may be mounted in a position at which it can detect the red blood cells (or the buffy coat) reaching a particular radius. The controller 190 may then monitor the output from the shoulder sensor to determine when the bowl 120 is full of red blood cells.

In some embodiments, the controller 190 may alternatively determine when the bowl 120 is full of red blood cells based upon the amount of whole blood drawn and the hematocrit of the whole blood. For example, the amount of red blood cells collected within the bowl 120 should be substantially equal to the volume of whole blood drawn from the source multiplied by the hematocrit of the drawn blood.

As mentioned above, the total amount of whole blood that may be safely withdrawn from a subject/patient is limited (e.g., typically 400 ml+/−10% or 450 ml+/−10%). As also discussed above, the volume of whole blood processed and the hematocrit value of the whole blood determines (along with the system efficiency) the volume of red blood cells that may be collected. For example, processing 400 ml whole blood with a hematocrit of 35% will yield less red blood cells than processing the same volume of whole blood with a hematocrit of 60%.

To that end, various embodiments of the system 100, take into account the maximum volume of whole blood that may be withdrawn (e.g., a target volume) as well as the target volume of red blood cells desired when processing whole blood (e.g., the maximum volume of the bowl 120). For example, in some embodiments of the present invention, as the controller 190 monitors the volume of whole blood drawn and the volume of red blood cells collected in the bowl 120 (e.g., based upon the output from the line sensor 14 or shoulder sensor), the controller 190 may compare the values to the target values. In other words, the controller 190 may compare the current volume of drawn whole blood to the target/maximum value (Step 460). Similarly, the controller 190 may monitor the output from the optical sensor 14 (or shoulder sensor) to determine when the bowl 120 is full of red blood cells (indicating that the target volume of red blood cells has been collected) (Step 465). If either the target volume of whole blood has been drawn from the source or the target volume of red blood cells has been collected (e.g., the bowl 120 is full of red blood cells), the controller 190 may stop drawing whole blood from the donor/source (Step 470) and stop the bowl 120 from spinning Once the controller 190 has stopped drawing whole blood and the bowl 120 has stopped spinning, the controller 190 may then transfer some or all the red blood cells contained within the bowl 120 to the RBC storage container 50 (e.g., by reversing draw pump P1 and drawing the red blood cells though tube 60, connector 58, tube 56, connector 54, valve V6, filter F4, tube 52 and into the RBC container 50) (Step 480). Accordingly, because the bowl 120 is stopped to collect the red blood cells, this system 100 is a discontinuous system.

As the controller 190 transfers the red blood cells within the bowl 120 to the RBC storage container 50, the system 100 may also introduce additive solution from the RBC additive solution container 65 into the red blood cells. For example, as discussed above, the controller 190 may energize pump P2 and draw additive solution from container 65, through valve V7, tube 71, and filter F5. The additive solution may then mix with the red blood cells being transferred at connector 58. Additionally or alternatively, the additive solution may be introduced into the bowl and mixed with the red blood cells within the bowl 120 prior to the transfer of the red blood cells to the RBC storage container 50.

It should be understood that, by monitoring the amount of whole blood drawn from the subject, monitoring the amount of red blood cells collected within the bowl 120, and stopping the draw step when a target value is reached for either, various embodiments of the present invention are able to maximize the amount of red blood cells collected yet ensure that the maximum allowable volume of whole blood is not exceeded. Additionally, unlike prior art systems, various embodiments of the present invention may be performed "chair-side" and are able to utilize a single fixed-volume bowl 120 which reduces the cost and complexity of the system. For example, unlike variable volume separation chambers, embodiments of the present invention that use fixed volume chambers do not require a separate control system to regulate chamber volume, are less expensive to manufacture, and have reduced procedure times.

Figure 5:
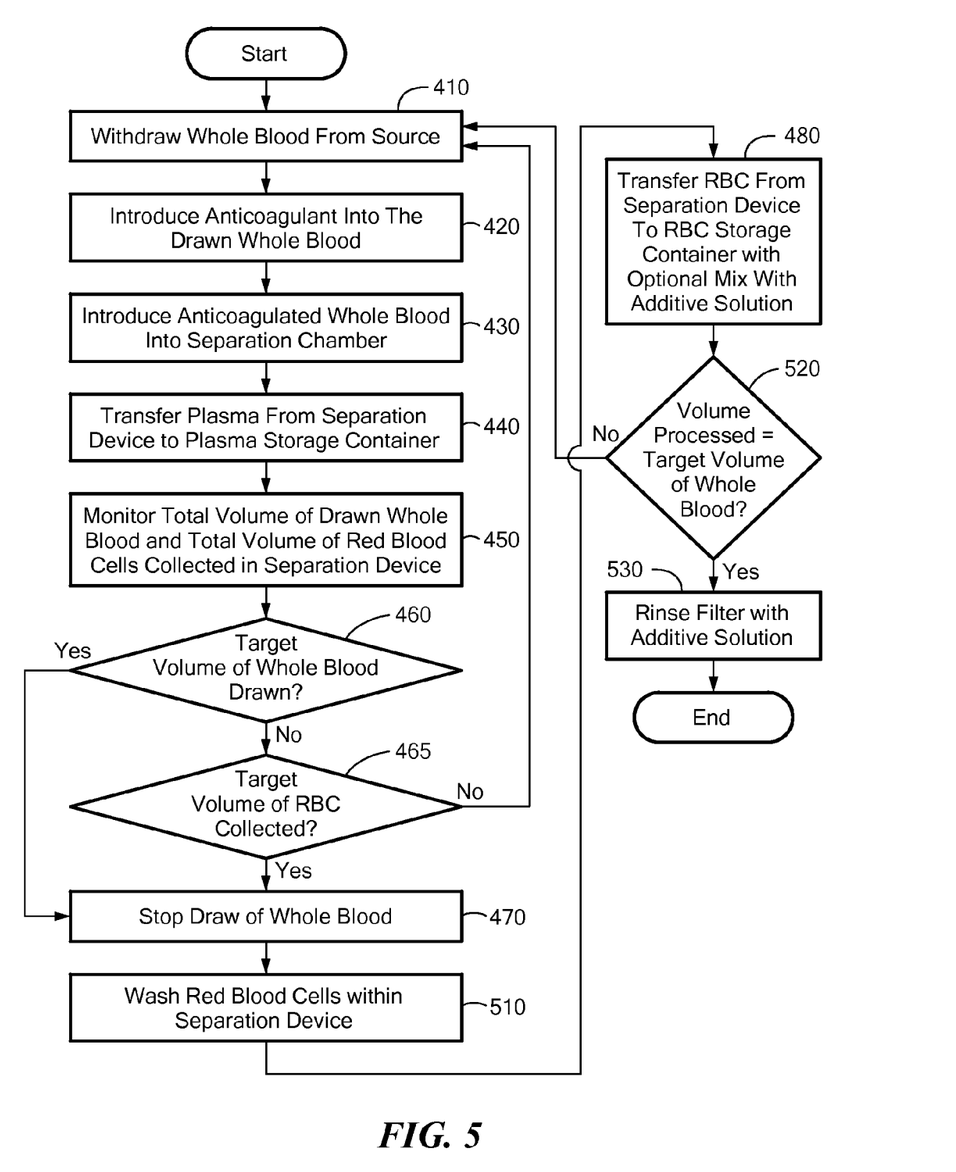
FIG. 5 is a flow chart depicting an alternative method for separating whole blood, in accordance with additional embodiments of the present invention.

In addition to the steps shown in FIG. 4, some embodiments of the present invention may have additional optional steps. For example, as shown in FIG. 5, prior to transferring the collected red blood cells to the RBC container 50, the system 100 may wash the red blood cells to remove proteins within the red blood cells (Step 510). To that end, the system 100/controller 190 may energize pump P2 to draw additive solution from container 65 through valve V7, line 71, filter F5, connector 58, and line 60 and into the bowl 120 (e.g., through inlet port PT1). As additional additive solution enters the bowl 120 (e.g., when the bowl 120 is spinning), the wash solution/protein mixture will be displaced from the bowl 120 through the outlet port PT2 and will be sent to the waste container 22 (e.g., through line 36, connector 72, valve V3, and line 39). Once the wash step is completed, the system 100 may then transfer the washed red blood cells within the separation device to the RBC storage container 50 (Step 480). During the transfer, the system 100 may also (optionally) add the additive solution required for storage of the red blood cells. It should be noted that, as the system 100 transfers the red blood cell/additive solution mixture, the mixture may pass through a leukoreduction filter F4 which, in turn, removes white blood cells (e.g., leukocytes) from the red blood cells.

Additionally, particularly for those embodiments in which the whole blood was first collected in a whole blood bag (e.g., those embodiments in which the source is a whole blood bag), after transferring the red blood cells to the RBC container 50, some embodiments may process additional whole blood in order to collect additional red blood cells if the total volume of whole blood processed is less than the target volume (or less than that collected within the whole blood bag) (Step 520). For example, the system 100/controller 190 may determine if there is sufficient whole blood remaining in the whole blood bag to start a second red blood cell collection cycle. If the system 100 determines there is a sufficient amount of whole blood, the system 100 may, once again, draw whole blood from the whole blood bag and into the bowl 120 and continue to process the whole blood in a manner similar to that described above until either the target volume of whole blood is reached or the target volume of red blood cells is collected within the bowl (for a second time) (e.g., the system may repeat steps 410, 420, 430, 440, 450, 460, 465, and 470).

In addition to or instead of determining if there is a sufficient volume of whole blood within the whole blood bag prior to drawing additional whole blood from the whole blood bag, the system 100 may determine whether there is a sufficient volume of red blood cells remaining within the whole blood bag. For example, the controller 190 can calculate the volume of red blood cells remaining within the whole blood bag based upon the volume of whole blood remaining (e.g., the initial volume of whole blood in the whole blood bag minus the volume of whole blood already drawn/processed) and the hematocrit of the whole blood (e.g., the volume of red blood cells remaining will be equal to the volume of whole blood remaining in the whole blood bag multiplied by the hematocrit of the whole blood). If the system 100/controller 190 determines there is a sufficient volume of red blood cells remaining within the whole blood bag, the system 100/controller 190 may start the second collection cycle.

Additionally, in order ensure that there is sufficient free volume in the bowl 120 to process the second cycle of whole blood, the system 100 may transfer some or all of the red blood cells within the bowl 120 to the red blood cell storage bag 50. For example, the system 100 may transfer all of the red blood cells to the storage bag 50 or the system 100 may transfer just enough red blood cells to accommodate the additional red blood cells that will be collected within the bowl 120 during the second cycle (e.g., the volume of red blood cells remaining in the whole blood bag).

Once the red blood cell/additive solution mixture is transferred to the RBC container 50, the system 100 may perform a rinse step to flush any red blood cells trapped in the filter F4 through the fitler F4 and into the RBC container 50 (Step 530). For example, the controller 190 may energize pump P2, and transfer additional additive solution (e.g., 70 mL) from container 65 through line 71, line 56, line 52, and through filter F4. As the additive solution passes through the filter F4, it flushes the trapped red blood cells out of the filter F4 and into the RBC container 50 which, in turn, increases the RBC recovery.

In some instances, various embodiments of the present invention may be able to increase the volume of plasma that is collected and/or increase the hematocrit of the final red blood cell product by adjusting/increasing the speed to the centrifuge bowl 120. For example, when processing whole blood with a relatively high hematocrit, the controller 190 may increase the speed of the centrifuge 110. By increasing the speed of the centrifuge 110, additional plasma may be separated from the incoming whole blood (e.g., the efficiency of the separation will be increased) and collected. Additionally, in some high hematocrit donors, the hematocrit of the final red blood cell product will increase (e.g., because the red blood cells within the bowl 120 will pack more tightly against the wall 127 of the bowl).

As discussed above, various bowl sizes may be used within the embodiments of the present invention. To that end, in some embodiments, it is desirable to choose a bowl 120 having a volume that is able to accommodate an appropriate volume of red blood cells (e.g., based on the hematocrit of the whole blood to be processed and the source of the whole blood). For example, for those embodiments in which the source is a whole blood bag, it is preferable to choose a bowl size that may accommodate the red blood cell volume of the lowest hematocrit donor. For those embodiments in which the source is a donor, it may be preferable to choose a bowl size that may hold the target volume of red blood cells (e.g., 180 ml). It is preferable that a bowl size is chosen that can accommodate from 150-210 ml of red blood cells, more preferably 160 to 200 ml of red blood cells, more preferably 170 to 190 ml of red blood cells, and most preferably around 180 ml of red blood cells.

However, in alternative embodiments, a smaller bowl 120 may be used. In such embodiments, the processing may occur in multiple steps. For example, the system 100 may draw a volume of whole blood (e.g., less than the target volume of whole blood), process the blood, and collect the red blood cells and plasma. The system 100 may then repeat the draw/processing steps until the target volume of whole blood is drawn or the target volume of red blood cells is collected.

The embodiments of the invention described above are intended to be merely exemplary; numerous variations and modifications will be apparent to those skilled in the art. All such variations and modifications are intended to be within the scope of the present invention as defined in any appended claims.

What is claimed is:
1. An apparatus for separating whole blood comprising:
an access device through which whole blood is drawn from a source;
a blood component separation device in which the drawn whole blood is separated into red blood cells and a second blood component;

a draw line fluidly connecting the venous access device and the blood component separation device;

a draw pump that draws whole blood from the source through the access device and draw line and into the blood component separation device;

a controller configured to control fluid flow through the apparatus, the controller also configured to control the operation of the draw pump and monitor a total volume of whole blood drawn from the source and a total volume of red blood cells collected within the blood component separation device, the controller configured to stop the draw pump when the first of a target whole blood volume is withdrawn or a target volume of red blood cells is collected within the blood component separation device.

2. An apparatus according to claim 1 further comprising: an optical sensor configured to monitor fluid flowing out of the blood component separation device and output a signal representative of the fluid.

3. An apparatus according to claim 2, wherein the controller is further configured receive the output signal and control operation of the draw pump based, at least in part, upon the output signal.

4. An apparatus according to claim 1, wherein the target whole blood volume is 400 mL.

5. An apparatus according to claim 1, wherein the target whole blood volume is 450 mL.

6. An apparatus according to claim 1, wherein the controller is further configured to determine the total volume of whole blood withdrawn based upon a number of revolutions of the draw pump.

7. An apparatus according to claim 1, wherein the source is a donor.

8. An apparatus according to claim 1, wherein the blood component separation device includes a centrifugal bowl.

9. An apparatus according to claim 8, wherein the centrifugal bowl has a volume sufficient to hold the target volume of red blood cells.

10. An apparatus according to claim 1, wherein the source is a whole blood storage container containing a volume of whole blood substantially equal to the target whole blood volume.

11. An apparatus according to claim 10, wherein the controller is further configured to restart the draw pump after a target volume of red blood cells is collected and if the whole blood storage container still contains whole blood.

12. An apparatus according to claim 10, wherein the controller is further configured to calculate a volume of red blood cells remaining in the whole blood storage container based, at least in part, upon a hematocrit value of the whole blood.

13. An apparatus according to claim 12, wherein the controller is configured to transfer a volume of red blood cells from the blood component separation device to the red blood cell storage container, the volume of red blood cells transferred being based upon the calculated volume of red blood cells remaining in the whole blood storage container.

14. An apparatus according to claim 13, wherein the controller is configured to restart the draw pump after the volume of red blood cells is transferred to the red blood cell storage container.

15. An apparatus according to claim 1, wherein the controller is configured to control a speed of the blood component separation device based, at least in part, upon a hematocrit value of the drawn whole blood.

16. An apparatus according to claim 15, further comprising a user input device configured to allow a user to input the hematocrit value.

17. An apparatus according to claim 1, further comprising: an additive solution container containing additive solution; an additive solution line fluidly connecting the additive solution container and the blood component separation device; and a second pump configured to draw additive solution from the additive solution container through the additive solution line and into the blood component separation device to wash the red blood cells within the blood component separation device.

18. An apparatus according to claim 17, wherein washing the red blood cells within the blood component separation device includes reducing protein concentration within the red blood cells.

19. A method for separating whole blood comprising:
drawing whole blood from a source;
introducing anticoagulant into the whole blood drawn from the source;
introducing, using a draw pump, the anticoagulated whole blood into a separation chamber;
separating in the separation chamber the whole blood into red blood cells and a second blood component, while blood is being drawn from the source;
monitoring a total volume of whole blood drawn from the source and a total volume of red blood cells collected within the separation chamber to determine when a target whole blood volume is drawn and when a target volume of red blood cells is collected within the separation chamber;
stopping, using a controller, the draw of whole blood from the source when the first of the target whole blood volume or target volume of red blood cells is reached.

20. A method according to claim 19 further comprising: monitoring, using an optical sensor, fluid flowing out of the separation chamber, the optical sensor outputting a signal representative of the fluid.

21. A method according to claim 20, wherein the controller receives the output signal and controls operation of the draw pump based, at least in part, upon the output signal.

22. A method according to claim 19, wherein the target whole blood volume is 400 mL.

23. A method according to claim 19, wherein the controller determines the total volume of whole blood withdrawn based upon the number of revolutions of the draw pump.

24. A method according to claim 19, wherein the source is a donor.

25. A method according to claim 19, wherein the separation chamber includes a centrifugal bowl.

26. A method according to claim 25, wherein the centrifugal bowl has a volume sufficient to hold the target volume of red blood cells.

27. A method according to claim 19, wherein the source is a whole blood storage container containing a volume of whole blood substantially equal to the target whole blood volume.

28. A method according to claim 27, further comprising: determining if whole blood remains within the whole blood storage container; and
restarting, if the whole blood storage container still contains whole blood, the draw pump after a target volume of red blood cells is collected.

29. A method according to claim 27, wherein the controller calculates a volume of red blood cells remaining in the whole blood storage container based, at least in part, upon a hematocrit value of the whole blood.

30. A method according to claim 29, wherein the controller transfers a volume of red blood cells from the separation chamber to the red blood cell storage container, the volume of red blood cells removed being based upon the calculated volume of red blood cells remaining in the whole blood storage container.

31. A method according to claim 30, wherein the controller restarts the draw pump after the red blood cells is transferred from the separation chamber.

32. A method according to claim 19, wherein the controller controls a speed of the separation chamber based, at least in part, upon a hematocrit value of the drawn whole blood.

33. A method according to claim 19, further comprising:
drawing additive solution from an additive solution container and into the separation chamber, the additive solution washing the red blood cells within the separation chamber as it enters the separation chamber.

34. A system for separating whole blood comprising:
means for drawing whole blood from a source;
means for introducing anticoagulant into the whole blood drawn from the source;
a blood component separation device for separating the drawn whole blood into red blood cells and a second blood component;
means for introducing the anticoagulated whole blood into the separation device;
means for monitoring a total volume of whole blood drawn from the source and a total volume of red blood cells collected in the separation device; and
a controlling means, in communication with the means for monitoring, for determining when a target whole blood volume is drawn and when a target volume of red blood cells is collected within the separation device, the controlling means configured to stop the draw of whole blood from the source when the first of the target whole blood volume and target volume of red blood cells is reached.

35. A system according to claim 34 further comprising:
a sensing means for monitoring fluid flowing out of the blood component separation device, the sensing means outputting a signal representative of the fluid flow out of the blood component separation device.

36. A system according to claim 35, wherein the controlling means receives the output signal and controls operation of the means for drawing based, at least in part, upon the output signal.

37. A system according to claim 34, wherein the target whole blood volume is between 400 and 500 mL.

38. A system according to claim 34, wherein the means for drawing whole blood includes a draw pump, the controlling means determining the total volume of whole blood drawn based upon a number of revolutions of the draw pump.

39. A system according to claim 34, wherein the source is a donor.

40. A system according to claim 34, wherein the blood component separation device includes a centrifugal bowl.

41. A system according to claim 40, wherein the centrifugal bowl has a volume sufficient to hold the target volume of red blood cells.

42. A system according to claim 40, wherein the centrifuge bowl has a volume that is smaller than the target volume of red blood cells.

43. A system according to claim 34, wherein the source is a whole blood storage container containing a volume of whole blood substantially equal to the target whole blood volume.

44. A system according to claim 43, wherein the controlling means is configured to restart the means for drawing after a target volume of red blood cells is collected in the separation chamber and if the whole blood storage container still contains whole blood.

45. A system according to claim 44, wherein the controlling means is configured to restart means for drawing after the blood component separation device is emptied.

46. A system according to claim 43, wherein the controlling means is configured to calculate a volume of red blood cells remaining in the whole blood storage container based, at least in part, upon a hematocrit value of the whole blood.

47. A system according to claim 46, wherein the controlling means is configured to transfer a volume of red blood cells from the blood component separation device to the red blood cells storage container, the volume of red blood cells transferred being based upon the calculated volume of red blood cells remaining in the whole blood storage container.

48. A system according to claim 34, wherein the controlling means controls a speed of the blood component separation device based, at least in part, upon a hematocrit value of the drawn whole blood.

49. A system according to claim 34, further comprising:
means for drawing additive solution from an additive solution container and into the blood component separation device, the additive solution washing the red blood cells within the blood component separation device as it enters the separation device.

* * * * *